United States Patent [19]

Kletschka et al.

[11] 4,009,719

[45] Mar. 1, 1977

[54] PROTECTIVE COVER FOR SUTURE BRIDGE

[75] Inventors: Harold D. Kletschka; Edson H. Rafferty, both of Minneapolis; Earl W. Clausen, Minnetonka, all of Minn.

[73] Assignee: Bio-Medicus, Inc., Minnetonka, Minn.

[22] Filed: May 12, 1975

[21] Appl. No.: 576,358

[52] U.S. Cl. .............................................. 128/335
[51] Int. Cl.² ........................................ A61B 17/04
[58] Field of Search .......... 128/132 R, 133, 334 R, 128/334 C, 335, 335.5

[56] References Cited

UNITED STATES PATENTS

| | | | |
|---|---|---|---|
| 3,014,483 | 12/1961 | McCarthy | 128/132 R X |
| 3,194,235 | 7/1965 | Cooke | 128/132 R |
| 3,456,965 | 7/1969 | Gajewski et al. | 128/334 C X |
| 3,628,813 | 12/1971 | Lee | 128/334 C X |
| 3,782,377 | 1/1974 | Rychlik | 128/132 R |
| 3,900,026 | 8/1975 | Wagner | 128/133 |
| 3,901,226 | 8/1975 | Scardenzan | 128/133 |

Primary Examiner—Richard J. Apley
Attorney, Agent, or Firm—Merchant, Gould, Smith, Edell, Welter & Schmidt

[57] ABSTRACT

For use with surgical suture bridges, a protective cover of generally flexible resilient material having smooth outer surfaces and disposed to cover sutures engaged and supported by a suture bridge, for protecting a suture from catching or rubbing on objects adjacent a surgical incision. Fastener devices on the cover are disposed to releasably hold the cover in enclosing relationship to an otherwise exposed portion of a suture.

10 Claims, 12 Drawing Figures

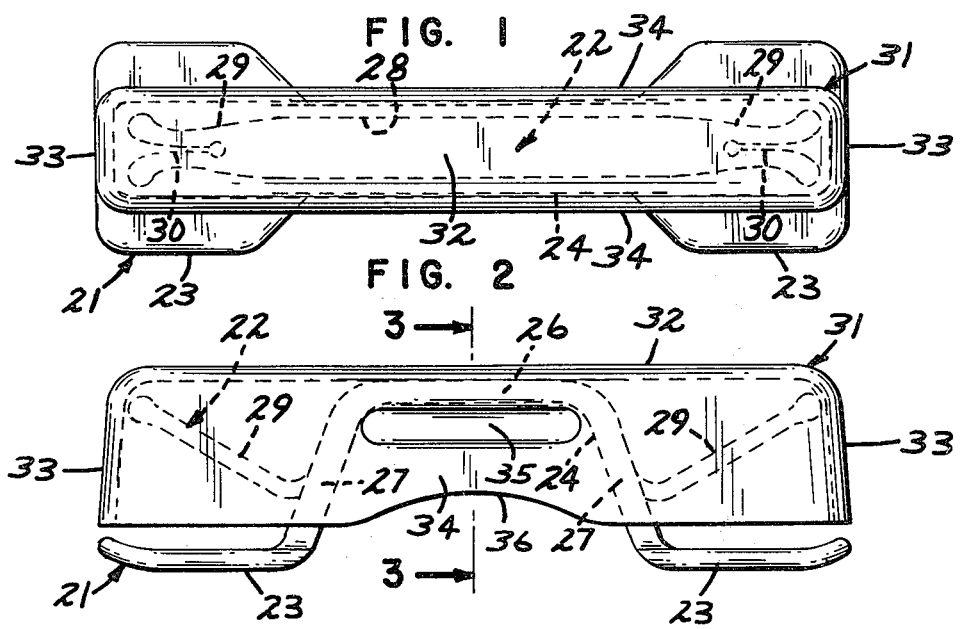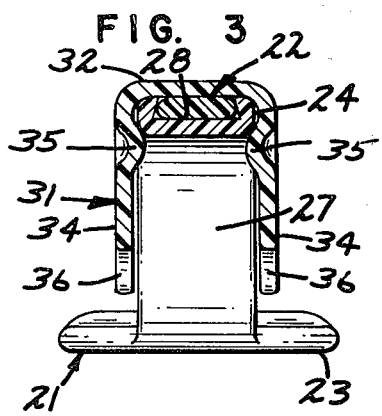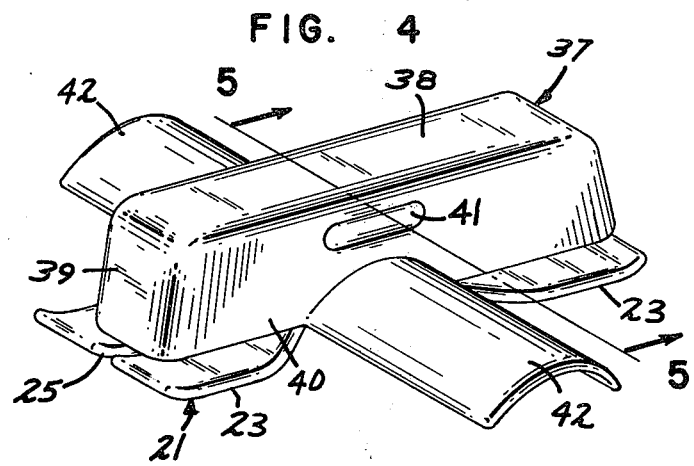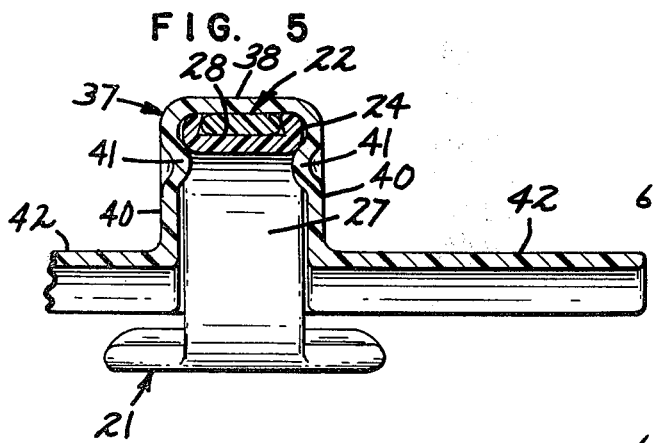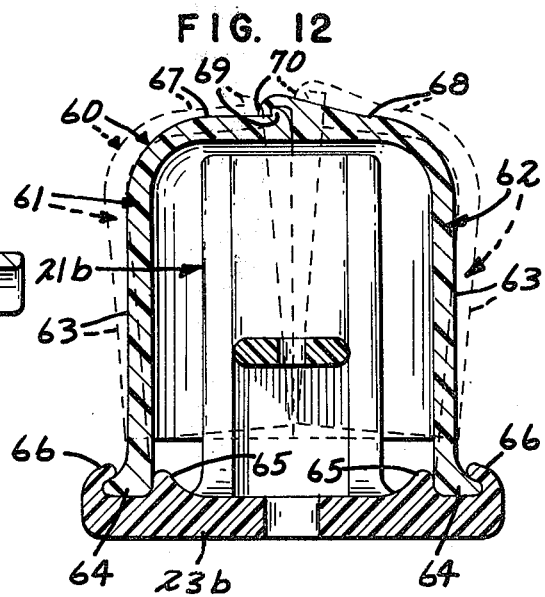

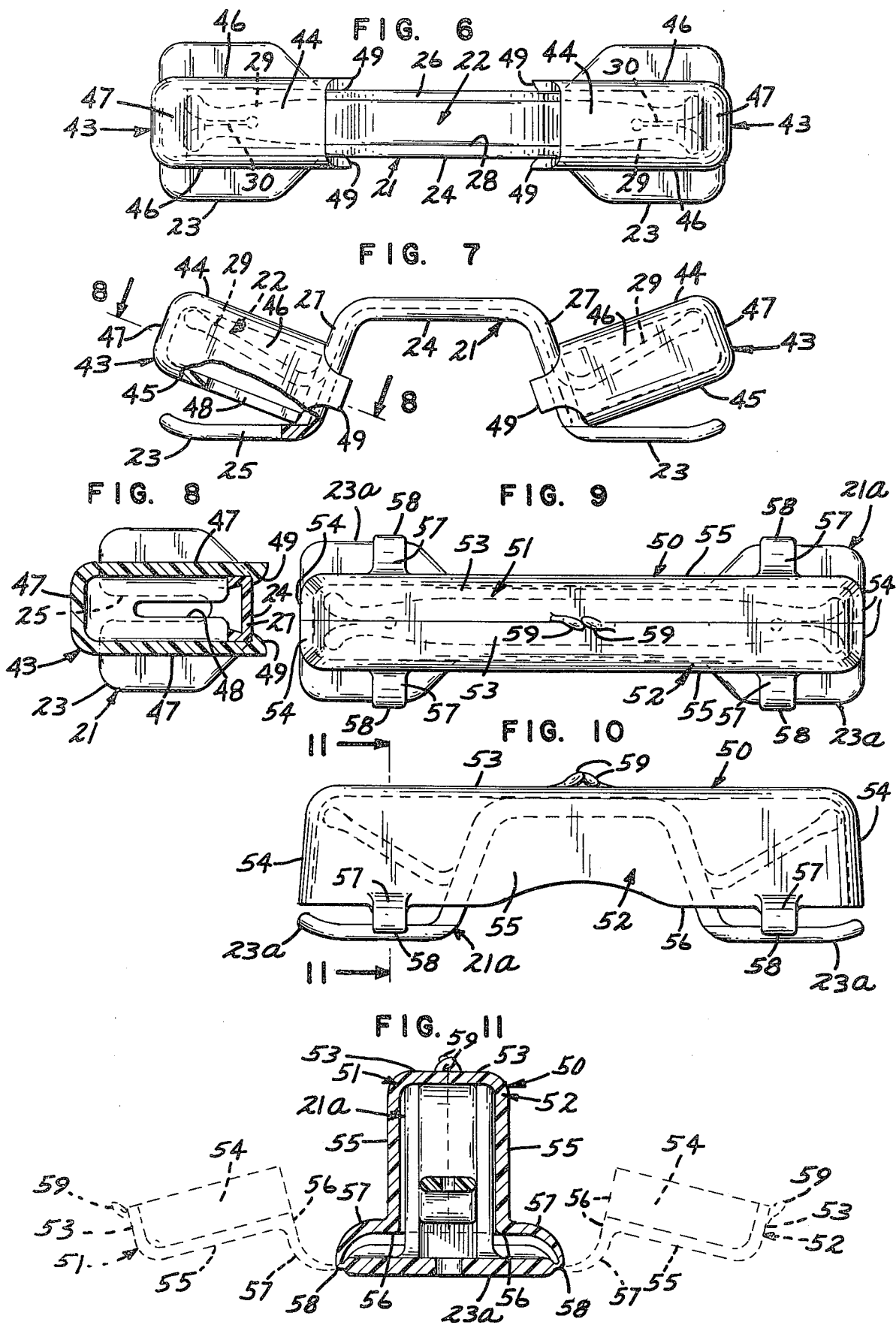

PROTECTIVE COVER FOR SUTURE BRIDGE

This invention relates generally to improvements in surgical devices and more particularly to aids in the prevention of the rubbing or catching of incision sutures on other objects, such as clothing, bed sheets or covers, and other articles.

The cover of this invention is particularly adapted for use with suture bridges designed to secure sutures above and out of contact with the incision closure and suture exit points while maintaining the sutures laterally fixed at the points where they exit to the skin. Several forms of suture bridges are disclosed in our prior U.S. Pat. No. 3,831,608, others being disclosed in such U.S. Pat. Nos. as Chambers, 815,264; Anderson, 1,852,098; McCarthy 3,014,483; Edwards et al, 3,650,274; and Chodorow, 3,695,271. While many of the suture bridges of these patents hold sutures against collateral displacement at their skin exit points, they do not have portions that project outwardly, or portions wherein the sutures or knots therein are exposed in such manner as to be caught or otherwise engaged by clothing, bed sheets or other covering, and possibly disturbed thereby to an extent as to cause irritation or pain to the patient. The protective cover of this invention, in its several forms herein disclosed, is highly effective in enclosing exposed portions of a suture, and is quickly and easily placed and releasably held in suture enclosing relationship on a suture bridge.

The protective cover is made from flexible resilient material to provide wall structure that is adapted to enclose the suture engaging portion of a bridge in outwardly spaced relation to those foot portions of the bridge that engage the skin of the patient laterally outwardly of the incision. The cover has smooth outer surfaces and snap fastener elements for releasably holding the cover in enclosing relationship to the suture engaging portion of the bridge.

DESCRIPTION OF THE DRAWINGS

FIG. 1 is a view in plan of a protective cover produced in accordance with this invention, and applied to a suture bridge;

FIG. 2 is a view in side elevation;

FIG. 3 is an enlarged transverse section taken on the line 3—3 of FIG. 2;

FIG. 4 is a view in perspective of a modified form of cover;

FIG. 5 is a fragmentary transverse section taken generally on the line 5—5 of FIG. 4;

FIG. 6 is a view corresponding to FIG. 1 but showing a further modification;

FIG. 7 is a view in side elevation of the structure of FIG. 6, some parts being broken away and some parts being shown in section;

FIG. 8 is a fragmentary section taken on the line 8—8 of FIG. 7;

FIG. 9 is a view corresponding to FIG. 1 but showing a still further modified form of cover;

FIG. 10 is a view in side elevation of the structure of FIG. 9;

FIG. 11 is a enlarged transverse section taken on the line 11—11 of FIG. 10;

FIG. 12 is a further enlarged transverse section corresponding to FIG. 11, but showing a further modified arrangement.

DETAILED DESCRIPTION OF THE PREFERRED EMBODIMENT

In FIGS. 1–8, a suture bridge is shown as comprising a lower bridge member 21 and an upper bridge member 22, the former including foot portions 23 interconnected by a bridge portion 24. Each foot portion 23 is provided with a slot 25 extending longitudinally of the bridge for passage therethrough of a suture. The bridge portion 24 includes a generally flat top section 26 and angular sections 27 that converge from the foot portions 23 toward the top portion 26. The top and angular portions 26 and 27 are formed to provide a dove tail channel or recess 28 for reception of the intermediate portion of the upper bridge member 22.

The upper bridge member 22 is formed to provide cantilevered arms or end portions 29 having longitudinal slots 30 which overlie respective ones of the slots 25 and are adapted to receive and have tied therein opposite end portions of a suture, not shown. Preferably, the arms 29 are resilient so as to maintain a suture under predetermined tension.

The suture bridge, above described, does not in and of itself comprise the instant invention. The suture bridge is more specifically disclosed and claimed in our copending application filed Aug. 6, 1974, Ser. No. 500,689 and entitled "Improved Suture Bridges".

A preferred embodiment of our protective cover is illustrated in FIGS. 1–3 and indicated generally at 31, the same comprising wall structure including an outer or top wall 32, opposite end walls 33, and laterally spaced generally parallel side walls 34, the cover having an open inner side or bottom. The several walls 32–34 are disposed to closely encompass the bridge members 21 and 22 above the foot portions 23 thereof, and to enclose the upper portions of sutures tied to the arms 29 of the upper bridge member 22. The cover 31 may be made from any suitable material having flexibility and resilience, such as polyethylene or other suitable synthetic plastic material. As shown in FIGS. 1–3, the cover 31 is formed to provide opposed snap fastener elements in the nature of detents 35 that are adapted to engage under the opposite sides thereof, the top ridge portion 26 to releasably hold the cover 31 in place on the bridge. Preferably, and as shown in FIGS. 1–3, the cover 31 has smooth outer surfaces and rounded corners, so as to slide smoothly over clothing, bed coverings, or other material which might come in contact therewith. The lower edges of the side walls 34 are upwardly arched, as indicated at 36 to avoid any contact with an underlying incision, should swelling occur at the incision. Further, the arched portions 36 provide clearance between the incision and the lower edge of the cover for the tips of an operator's fingers, for the purpose of spreading the side walls 34 to disengage the dentents 35 from the bridge and remove the cover therefrom when the incision has healed to the point where removal of the suture is desired.

MODIFICATIONS OF THE PREFERRED EMBODIMENT

In the modified form illustrated in FIGS. 4 and 5, a cover 37 is substantially identical in shape to the cover 31, having a top wall 38, opposite end walls 39, one of which is shown, and opposite side walls 40 provided with opposed detents 41. Like the cover 31, the cover 37, when mounted on a suture bridge, is disposed to extend transversely of an underlying incision. In the form of cover illustrated in FIGS. 4 and 5, the side walls 40 are formed to provide foot portions 42 that extend transversely outwardly from the walls 40 to overlie and protect portions of an incision at opposite sides of the bridge on which the cover 37 is mounted. Preferably, the foot portions 42 are cross sectionally curved, and the corners and edges thereof are rounded so as to provide smooth outer surface portions that do not catch on clothing, bed sheets and the like.

A pair of covers are illustrated in FIGS. 6–8, these being identical in construction, and used in pairs, each cover being indicated generally at 43. As shown, each cover 43 comprises top and bottom walls 44 and 45 respectively, opposite flat side walls 46 and outer end walls 47, the inner ends of the covers 43 being open. The bottom walls 45 are provided with slot like openings 48, each of which is adapted to overlie the slot 25 in an underlying foot portion 23 of the bridge, see particularly FIG. 8. Like the covers 31 and 37, the covers 43 are preferably made from flexible resilient material and have smooth outer surfaces and rounded edges and corners, the inner ends of the covers 43 having marginal edges. The side walls 46 have portions extending longitudinally beyond the marginal edges to provide snap fastener elements in the nature of latch hooks 49 that have latching engagement with the inner side surfaces of the angular portions 27 of the lower bridge member 21.

In the form of the invention illustrated in FIGS. 9–11, a cover, indicated generally at 50, comprises a pair of cooperating cover sections 51 and 52 each having an outer or top wall portion 53, opposite end wall portions 54 and a side wall 55. Each side wall 55 has integrally formed therewith, adjacent its inner marginal edge 56, a pair of spaced foot portions 57 that extend laterally outwardly and downwardly from the marginal edge 56 and decreasing in thickness to provide relatively thin flexible hinge portions 58 integrally formed with or anchored to foot portions 23a of a lower bridge member 21a. With the exception of the hinge portions 58 attached to the foot portions 23a, the lower bridge member 21a is identical to the bridge member 21. As shown in FIG. 11, the cover sections 51 and 52 are movable on their hinge portions 58 between cover open positions shown by dotted lines in FIG. 11, and longitudinally abutting cover closed positions shown by full lines in FIG. 11. The cover sections 51 and 52 are releasably held in their cover closed positions by snap fastener buttons 59 integrally formed with the outer or top wall portions 53 of respective cover sections 51 and 52. The snap fastener buttons 59 are preferably of the type found on the hinged closure portions of coin purses and ladies hand bags.

In the modified arrangement illustrated in FIG. 12, a cover 60 is similar to the cover 50 differing therefrom only in the manner of hinging the same to the foot portions of the suture bridge, and in the design of the snap fastener. The cover 60 comprises cooperating cover sections 61 and 62 the side walls 63 of which are provided with downwardly projecting foot portions 64 that are mounted in socket forming heel and toe elements 65 and 66 respectively, integrally formed with foot portions 23b, one of which is shown, of a lower bridge member 21b, that is otherwise identical to the lower bridge member 21. Although only one foot portion 64 is shown as being associated with each side wall 63 and but one foot portion 23b is shown in FIG. 12, it will be understood that each side wall 63 is provided with a pair of foot portions 64 each associated with heel and toe elements 65 and 66 of both foot portions 23b of the suture bridge member 21b. The cover sections 61 and 62 have top wall portions 67 and 68 respectively, these being provided with cooperating snap fastener hooks 69 and 70 for releasably holding the cover sections 61 and 62 in cover closed positions shown by full lines in FIG. 12. The foot portions 64 are so disposed, relative to their respective side walls 63 that, when the hooks 69 and 70 are disengaged, the cover sections 61 and 62 assume a normally spread apart relationship as indicated by dotted lines in FIG. 12. When the cover sections 61 and 62 are moved in to cover closed relationship, as shown by full lines in FIG. 12, the sections are under yielding bias toward a cover open relationship. After the cover sections 61 and 62 are unlatched, they may be manually moved away from each other beyond their normally spread apart portions and the foot portions 64 pivotally moved out of engagement with their respective heel and toe portions 65 and 66. Thus, the cover sections 61 and 62 can be entirely disassociated from the suture bridge during the suturing operation, and can be thereafter quickly and easily applied to the suture bridge.

While we have shown and described a preferred embodiment and several modified forms of protective cover for suture bridges, it will be understood that the same is capable of further modification without departure from the spirit and scope of the invention, as defined in the claims.

What is claimed is:

1. A cover for surgical bridges of the type comprising spaced apart skin-engaging foot portions joined by a bridge portion for supporting incision sutures under tension; said cover having wall structure adapted to enclose a suture engaging portion of a bridge in outwardly spaced relation to the foot portions of the bridge, said wall structure including a generally flat top wall, opposed generally flat side walls, and at least one end wall, said cover walls having smooth outer surfaces and rounded corners, said cover including snap fastener elements for releasably holding said cover in enclosing relationship to said sature engaging portion of the bridge.

2. The cover according to claim 1 in which said wall structure is flexible and resilient, said snap fastener elements being integral with said wall structure.

3. The cover according to claim 2 in which said snap fastener elements comprise opposed detents in said opposite walls.

4. The cover according to claim 3 in which said side walls are elongated and disposed to extend transversely of an incision when mounted on a surgical suture bridge, each of said side walls having a hood portion extending transversely outwardly therefrom to overlie portions of the incision at opposite sides of the bridge 5. The cover according to claim 2 in which said wall structure includes opposite side walls and end walls defining a marginal edge, said snap fastener elements including latch hooks projecting outwardly of said marginal edge at each of said opposite side walls.

6. The cover according to claim 2 in which said wall structure comprises a pair of cooperating cover sections each having portions for anchoring engagement with the suture bridge, said cover sections being pivotally movable between cover open and closed positions relative to each other, said snap fastener elements being disposed one on each of said cover sections for cover locking interengagement, when said cover sections are moved to their closed positions.

7. In combination with a surgical bridge for supporting incision sutures under tension and including spaced-apart foot portions adapted to engage the surface of a patient's skin on opposite sides of an incision and joined by a connecting portion shaped to be spaced from the incision; a cover having wall structure adapted to enclose a suture engaging portion of the bridge in outwardly spaced relation to said foot portions, said cover having a smooth outer surface and a portion engaging said bridge, said wall structure including a generally flat top wall, opposed generally flat side walls, at least one end wall, and snap fastener elements for releasably holding said cover in enclosing relationship to said suture portion and suture engaged thereby.

8. The combination according to claim 7 in which said snap fastener elements comprise opposed detents in side walls and engaging opposite sides of said connecting portion.

9. The cover according to claim 7 in which said cover includes opposite flexible resilient side walls, said snap fastener elements comprising a pair of latch hooks on said side walls and disposed for hooking engagement with said bridge.

10. The cover according to claim 7 in which said wall structure comprises a pair of cooperating cover sections each having portions for anchoring engagement with the suture bridge, said cover sections being pivotally movable between cover open and closed positions relative to each other, said snap fastener elements being disposed one on each of said cover sections for cover locking interengagement, when said cover sections are moved to their cover closed positions.

* * * * *